US010588951B2

(12) United States Patent
Holmdahl et al.

(10) Patent No.: US 10,588,951 B2
(45) Date of Patent: Mar. 17, 2020

(54) COMPOUND COMPRISING AN AUTOANTIGENIC PEPTIDE AND A CARRIER WITH A MHC BINDING MOTIF

(71) Applicant: FRAUNHOFER-GESELLSCHAFT ZUR FORDERUNG DER ANGEWANDTEN FORSCHUNG E.V., München (DE)

(72) Inventors: Rikard Holmdahl, Lund (SE); Jan Kihlberg, Pixbo (SE); Balik Dzhambazov, Plovdiv (BG); Mikael Vestberg, Sodra Sandby (SE)

( * ) Notice: Subject to any disclaimer, the term of this patent is extended or adjusted under 35 U.S.C. 154(b) by 246 days.

(21) Appl. No.: 14/658,962

(22) Filed: Mar. 16, 2015

(65) Prior Publication Data

US 2015/0231216 A1 Aug. 20, 2015

Related U.S. Application Data

(63) Continuation of application No. 12/092,724, filed as application No. PCT/SE2006/001290 on Nov. 15, 2006, now abandoned.

(60) Provisional application No. 60/758,481, filed on Jan. 12, 2006.

(30) Foreign Application Priority Data

Nov. 17, 2005 (SE) ...................... 0502530

(51) Int. Cl.
| A61K 39/00 | (2006.01) |
| A61K 47/64 | (2017.01) |
| C07K 14/705 | (2006.01) |
| C07K 7/08 | (2006.01) |
| C07K 14/47 | (2006.01) |
| C07K 14/74 | (2006.01) |
| C07K 16/18 | (2006.01) |
| A61K 47/68 | (2017.01) |

(52) U.S. Cl.
CPC ...... *A61K 39/0008* (2013.01); *A61K 47/6425* (2017.08); *A61K 47/6811* (2017.08); *A61K 47/6843* (2017.08); *C07K 7/08* (2013.01); *C07K 14/4713* (2013.01); *C07K 14/705* (2013.01); *C07K 16/18* (2013.01); *A61K 2039/605* (2013.01); *A61K 2039/6056* (2013.01); *C07K 2319/33* (2013.01)

(58) Field of Classification Search
None
See application file for complete search history.

(56) References Cited

U.S. PATENT DOCUMENTS 6,451,314 B1 9/2002 Clark

FOREIGN PATENT DOCUMENTS

| WO | 1996040944 A2 | 12/1996 |
| WO | 1998005684 A2 | 2/1998 |
| WO | 2001036448 A2 | 5/2001 |

OTHER PUBLICATIONS

Von Delwig et al (Arthritis & Rheumatism, Feb. 2006, 54(s): 482-491) (Year: 2006).*
Rammensee et al (MHC Ligands and Peptide Motifs, 1997, Landes Bioscience, Austin, Texas, pp. 300-301) (Year: 1997).*
Nelson et al (PNAS, 1993, 90: 1227-1231) (Year: 1993).*
Kalandadze et al (J. Biol. Chem. 1996, 271 (33), 20156-20162) (Year: 1996).*
Cresswell, P (Annual Rev. Immunol. 1994, 12: 259-293) (Year: 1994).*
Latham et al (J. Immunol. Jan. 4, 2005, 174: 3978-3985) (Year: 2005).*
Holm, et. al., "An Improved Synthesis of a Galactosylated Hyroxylysine Building Block and it use in Solid-Phase Glycopeptide Synthesis," Tetrahedron, 2000, vol. 56, pp. 1579-1586.
Dzhambazov, et. al., "Therapeutic Vaccination of Active Arthritis with a Glycosylated Collagen Type II Peptide in Complex with MHC Class II Molecules 1," The Journal of Immunology, 2006, vol. 176, pp. 1525-1533.
Bäcklund et al. "Glycosylation of type II collagen is of major importance for T cell tolerance and pathology in collagen-induced arthritis." European Journal of Immunology. 2002. 32(12):3776-84.
Bäcklund et al. "Predominant selection of T cells specific for the glycosylated collagen type II epitope (263-270) in humanized transgenic mice and in rheumatoid arthritis." Proceedings of the National Academy of Sciences of the USA.2002. 99(15) 9960-9965.
Broddefalk et al. "T cells recognize a glycopeptide derived from type II collagen in a model for rheumatoid arthritis." Journal of the American Chemical Society. 1998. 120(31), 7676-7683.
Broddefalk et al. "Use of acid-labile protective groups for carbohydrate moieties in synthesis of glycopeptides related to type II collagen." Tetrahedron. 1998. 54, 12047-12070.
Corthay et al. "Epitope glycosylation plays a critical role for T cell recognition of type II collagen in collagen-induced arthritis." European Journal of Immunology. 1998. 28(8), 2580-2590.
Dzhambazov et al. "The major T cell epitope on type II collagen is glycosylated in normal cartilage but modified by arthritis in both rats and humans." European Journal of Immunology. 2005. 35(2), 357-366.

(Continued)

*Primary Examiner* — G. R. Ewoldt
*Assistant Examiner* — Marianne DiBrino
(74) *Attorney, Agent, or Firm* — SAFFIRE IP; Daren P. Nicholson

(57) ABSTRACT

The invention relates a compound comprising (a) a peptide and (b) a carrier, wherein said peptide having at least the motif X-X-X-X-X-X-X, wherein at least one amino acid residue X is glycosylated, said peptide being linked to the peptide binding protein and said carrier comprises at least a MHC binding motif being linked to said peptide as well as pharmaceutical compositions comprising said compound and the use of said compound or pharmaceutical composition for the treatment of a disease, such as an inflammatory joint disease. The subject matter of the application is exemplified with peptides derived from type II collagen such as peptides having at least the sequence AGFKGEA, or IAG-FKGEQPKG, or the peptide AAAKAAA. Preferably a hydroxylysine in the peptides are glycosylated.

10 Claims, 6 Drawing Sheets

Specification includes a Sequence Listing.

(56) References Cited

OTHER PUBLICATIONS

Holm et al. "Glycopeptide specificity of helper T cells obtained in mouse models for rheumatoid arthritis." Chembiochem. 2002 3(12), 1209-1222.
Kjellén et al. "The structural basis of MHC control of collagen-induced arthritis; binding of the immunodominant type II collagen 256-270 glycopeptide to H-2Aq and H-2Ap molecules." European Journal of Immunology. 1998. 28(2):755-767.
Malmström et al. "T cells that are naturally tolerant to cartilage-derived type II collagen are involved in the development of collagen-induced arthritis." Arthritis Research. 2000. 2, 315-326.
Michaëlsson et al. "Antigen processing and presentation of a naturally glycosylated protein elicits major histocompatibility complex class II-restricted, carbohydrate-specific T cells." European Journal of Immunology. 1996. 26(8):1906-1910.
Michaëlsson et al. "Identification of an immunodominant type-II collagen peptide recognized by T cells in H-2q mice: self tolerance at the level of determinant selection." European Journal of Immunology. 1992. 22(7): 1819-1825.
Michaëlsson et al. "T cell recognition of carbohydrates on type II collagen." Journal of Experimental Medicine. 1994. 180(2), 745-749.
Myers et al. "Characterization of a tolerogenic T cell epitope of type II collagen and its relevance to collagen-induced arthritis." Journal of Immunology. 1992. 149: 1439-1443.
Zuo et al. "A single-chain class II MHC-IgG3 fusion protein inhibits autoimmune arthritis by induction of antigen-specific hyporesponsiveness." Journal of Immunology. 2002. 168(5):2554-2559.
Broddefalk et al. "Preparation of a diglycosylated hydroxylysine building block used in ssolid-phase synthesis of a glycopeptide from type II collagen." Journal of Organic Chemistry. 1999. 64, 8948-8953.
Myers, "Peptide-Induced Suppression of Collagen-Induced Arthritis in HLA-DR1 Transgenic Mice," American College of Theumatology, vol. 46, No. 12, Dec. 2002, pp. 3369-3377.
Holmdahl, R., Carlsen, S., Mikulowska, A., Vestberg, M., Brunsberg, U., Hansson, A.-S., Sundvall, M., Jansson, L. & Pettersson, U., "Genetic Analysis of Mouse Model" (1998) in Human Genome Methods, ed. Adolpho, K. W. (CRC press, New York), pp. 215-238.
Aho, K., Palosuo, T., Raunio, V., Puska, P., Aromaa, A. & Salonen, J. T., "When does rheumatoid arthritis start?" (1985) Arthritis Rheum 28, 485-489.
Rantapaa-Dahlqvist, S., de Jong, B. A., Berglin, E., Hallmans, G., Wadell, G., Stenlund, H., Sundin, U. & van Venrooij, W. J., "Antibodies against cyclic citrullinated peptide and IgA rheumatoid factor predict the development of rheumatoid arthritis" (2003) Arthritis Rheum 48, 2741-9.
Berglin, E., Padyukov, L., Sundin, U., Hallmans, G., Stenlund, H., Van Venrooij, W. J., Klareskog, L. & Dahlqvist, S. R., "A combination of autoantibodies to cyclic citrullinated peptide (CCP) and HLA-DRB1 locus antigens is strongly associated with future onset of rheumatoid arthritis" (2004) Arthritis Res Ther 6, R303-8.
Van Gaalen, F. A., Van Aken, J., Huizinga, T. W., Schreuder, G. M., Breedveld, F. C., Zanelli, E., van Ven-rooij, W. J., Verweij, C. L., Toes, R. E. & de Vries, R. R., "Association between HLA class II genes and autoantibodies to cyclic citrullinated peptides (CCPs) influences the severity of rheumatoid arthritis" (2004) Arthritis Rheum 50, 2113-21.
Corrigall, V. M., Bodman-Smith, M. D., Fife, M. S., Canas, B., Myers, L. K., Wooley, P., Soh, C, Staines, N. A., Pappin, D. J., Berlo, S. E., van Eden, W., van Der Zee, R., Lanchbury, J. S. & Panayi, G. S. (2001) J Immunol 166, 1492-8.
Fritsch, R., Eselbock, D., Skriner, K., Jahn-Schmid, B., Scheinecker, C, Bohle, B., Tohidast-Akrad, M., Hayer, S., Neumuller, J., Pinal-Roma, S., Smolen, J. S. & Steiner, G., "Characterization of Autoreactive T Cells to the Autoantigens Heterogeneous Nuclear Ribonucleoprotein A2 (RA33) and Filaggrin in Patients with Rheumatoid Arthritis" (2002) J Immunol 169, 1068-76.
Cook, A. D., Rowley, M. J., Mackay, I. R., Gough, A. & Emery, P., "Antibodies to Type II Collagen in Early Rheumatoid Arthritis" (1996) Arthritis Rheum 39, 1720-1727.
Holm, B., Baquer, S. M., Holm, L, Holmdahl, R. & Kihlberg, J., "Role of the Galactosyl Moiety of Collagen Glycopeptides for T-Cell Stimulation in a Model for Rheumatoid Arthritis," (2003) Bioorganic and Medicinal Chemistry 11, 3981-7.
Scott, C. A., Garcia, K. C, Carbone, F. R., Wilson, I. A. & Teyton, L., "Role of Chain Pairing for the Production of Functional Soluble IA Major Histocompatibility Complex Class II Molecules" (1996) J Exp Med 183, 2087-95.
Bunch, T. A., Grinblat, Y. & Goldstein, L. S., "Characterization and use of the *Drosophila* metallothionein promoter in cultured *Drosophila melanogaster* cells" (1988) Nucleic Acids Res 16, 1043-61.
Andersson, M. & Holmdahl, R., "Analysis of type II collagen-reactive T cells in the mouse. I. Different regulation of autoreactive vs. non-autoreactive anti-type II collagen T cells in the DBA/1 mouse" (1990) Eur J Immunol 20, 1061-1066.
Broddefalk, J., Backlund, J., Almqvist, F., Johansson, M., Holmdahl, R. & Kihlberg, J., "T Cells Recognize a Glycopeptide Derived from Type II Collagen in a Model for Rheumatoid Arthritis" (1998) J Am Chem Soc 120, 7676-7683.
Holmdahl, R., Klareskog, L., Andersson, M. & Hansen, C., "High antibody response to autologous type II collagen is restricted to H-2q" (1986) Immunogenetics 24, 84-89 (Abstract only).
Dzhambazov, Nandakumar, Kihlberg, Fugger, Holmdahl, and Vestberg. Therapeutic vaccination of active arthritis with a glycosylated collagen type II peptide in complex with MHC class II molecules. J Immunol 2006, 176: 1525-1533.
Raposo, Merky, Lundqvist, Yamada, Urbonaviciute, Niaudet, Viljanen, Kihlberg, Kyewski, Ekwal, Holmdahl, and Bäcklund, T cells specific for post-translational modifications escape intrathymic tolerance induction. 2018, Nature Communications 9 (1): 353.
Ponchel et al., "CD4+ T-cell subsets in rheumatoid arthritis," Int. J. Clin. Rheumatol. (2012) 7(1), 37-53.
Van Eden et al., "Cloning of the mycobacterial epitope recognized by T lymphocytes in adjuvant arthritis," Nature 331; 171-172 Jan. 14, 1988.
Van Eden et al., "Arthritis induced by a T-lymphocyte clone that responds to *Mycobacterium tuberculosis* and to cartilage proteoglycan," PNAS 1985; 5117-5120, Abstract.
Vanderlugdt et al., "Epitope spreading in immune-mediated diseases: implications for immunotherapy," Nature Reviews Immunology 2, 85-95 (2002) Abstract.
Vanderlugdt et al., "Epitope Spreading," Current Opinion in Immunology, vol. 8, Issue 6, Dec. 1996, pp. 831-836, Abstract.
Bajtner et al., "Chronic development of collagen-induced arthritis is associated with arthritogenic antibodies against specific epitopes on type II collagen," Arthritis Research & Therapy vol. 7 No. 5 2005.
Bevaart et al., "Evaluation of Therapeutic Targets in Animal Models of Arthritis," Arthritis & Rheumatism. 62, 2192-2205 (2010).
Freysdottir, "Mucosal tolerance to KLH reduces BSA-induced arthritis in rats—an indication of bystander suppression," J Clin Immunol. May 2007;27(3):284-93 Abstract.
"Adjuvant Induced Arthritis—Adjuvants," Chondrex, www.chondrex.com/animal-models/adjuvant-induced-arthritis-adjuvants (screenshot Jun. 6, 2019).
May 14, 2014 Canadian Intellectual Property Office Office Action in CA 2,629,881 to Rikard Holmdahl et al. national entry date May 14, 2008 from PCT/SE2006/001290 filed Nov. 15, 2006, A Compound Comprising an Autoantigenic Peptide and a Carrier with a MHC Binding Motif.
Apr. 8, 2015 Canadian Intellectual Property Office Office Action in CA 2,629,881 to Rikard Holmdahl et al. national entry date May 14, 2008 from PCT/SE2006/001290 filed Nov. 15, 2006, A Compound Comprising an Autoantigenic Peptide and a Carrier with a MHC Binding Motif.

\* cited by examiner

COMPOUND COMPRISING AN AUTOANTIGENIC PEPTIDE AND A CARRIER WITH A MHC BINDING MOTIF

FIELD OF INVENTION

The invention relates a compound comprising (a) a peptide and (b) a carrier, wherein said peptide having at least the motif X-X-X-X-X-X-X, wherein at least one amino acid residue X is glycosylated, said peptide being linked to the peptide binding protein and said carrier comprises at least a MHC binding motif being linked to said peptide as well as pharmaceutical compositions comprising said compound and the use of said compound or pharmaceutical composition for the treatment of a disease, such as an inflammatory joint disease.

BACKGROUND OF INVENTION

There is an increasing population of humans suffering from different kinds of inflammatory joint diseases. Diseases, which sometimes are impossible to cure, where the treatment is lifelong and where the symptoms often become worse during the years. So far the focus of the treatment has been on trying to find compounds, which reduce the symptoms but not cure the disease or make the disease decline.

One example of such a disease is rheumatoid arthritis (RA), which is characterized by chronic inflammation of the articular synovial tissues initiated by leukocyte infiltration (mainly neutrophils, macrophages and T cells) and secretion of inflammatory cytokines (TNF-alpha, IFN-gamma, IL-I, IL-6), chemokines and destructive enzymes such as matrix metalloproteases. Activation of T cells is believed to be an important pathogenic factor in the disease although its exact role and potential as a therapeutic target has not yet been identified. The abnormal activation of T cells do, however, most likely occur years before the clinical diagnosis of the disease as T cell dependent IgG antibodies specific for immunoglobulin Fc (i.e rheumatoid factors) and citrullinated protein epitopes are highly predictive for disease (1, 2). Importantly, the risk for developing arthritis is dramatically increased in individuals who have both such antibodies and express certain MHC class II molecules, that share a specific peptide pocket, the so called MHC shared epitope (3, 4). The MHC class II region is also the strongest known genetic factor associated with RA. Taken together, these findings argue for a pathogenic role of MHC class II restricted autoreactive T cells. It has however been difficult to identify a single specificity of such T cells although T cell reactivity to several autoantigens, such as BiP, RA33 and GPI and also joint specific antigens such as type II collagen (CII), have been reported (5-8).

Since there is no way to cure inflammatory joint diseases today there is a need for developing a way to cure the disease.

SUMMARY OF THE INVENTION

The object of the present invention is to solve the above, discussed problem in connection with inflammatory joint diseases.

It has surprisingly been found that by the use of a compound comprising (a) a peptide and (b) a carrier, wherein said peptide having at least the motif X-X-X-X-X-X-X, wherein at least one amino acid residue X is glycosylated, said peptide being linked to the peptide binding protein and said carrier comprises at least a MHC binding motif being linked to said peptide it is possible for the first time to reduce and/or eliminate an inflammatory joint disease. Thereby a mammal suffering from such a disease will bee cured or at least the disease will be reduced.

Additionally the invention relates to a pharmaceutical composition comprising said compound as well as the use of said compound for the treatment of an inflammatory disease or disorder, such as arthritis, rheumatoid arthritis, ankylosing spondylitis, psoriasis arthritis, osteoarthritis, relapsing polychondritis and Menieres disease In a specific embodiment, said compound is used to vaccinate a mammal and thereby cure or prevent an inflammatory disease or disorder.

Further advantages and objects with the present invention will be described in more detail, inter alia with reference to the accompanying drawings.

DETAILED DESCRIPTION OF THE INVENTION

Figure 1:
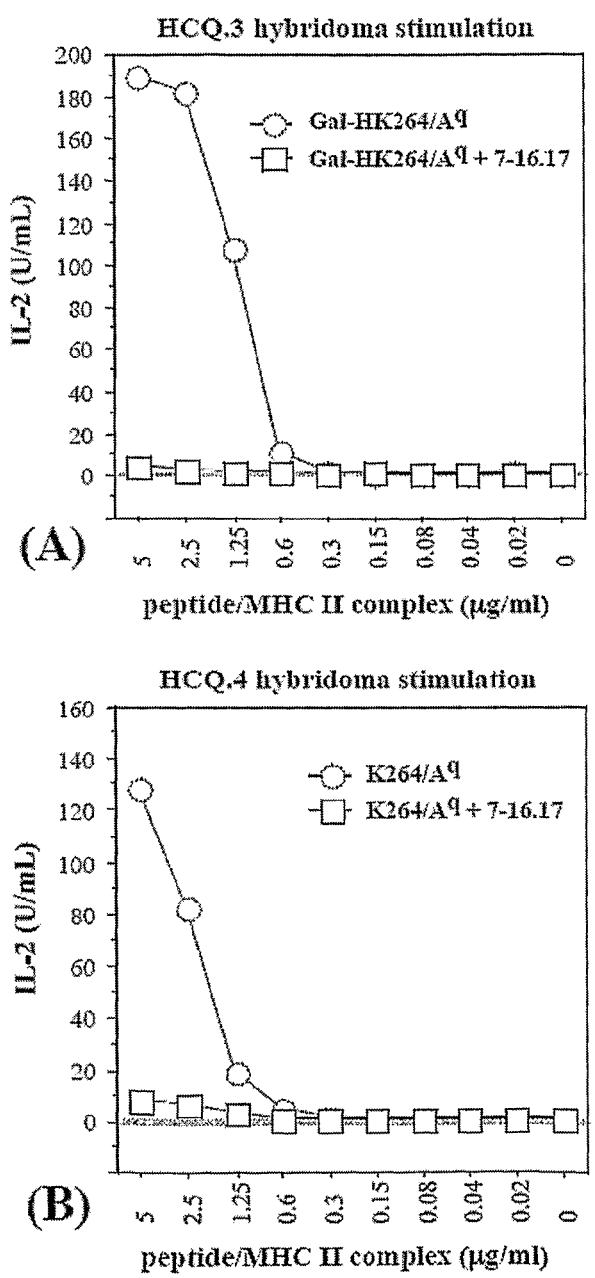
FIG. 1 shows peptide/$A^q$ complexes activate antigen-specific T-cell hybridomas.
(A) HCQ.3 hybridoma, specific for GalOK264 CII259-273 epitope; (B) HCQ.4 hybridoma, specific for non-modified (K264) CII259-273 epitope.

Definitions
In the context of the present application and invention the following definitions apply:

The term "MHC class II molecule" is intended to mean a protein consisting of an alpha and a beta chain, coded from two distinct genes. This protein is normally cell surface bound on so-called antigen presenting cells (APC) and serve as a receptor for peptides. The peptide is bound to a specific site, the peptide binding site, in the MHC molecule and the resulting protein structure (the peptide bound to the two chain MHC class II molecule) is recognized by the T cell receptor.

This interaction is the crucial molecular and antigen specific event in the immune response and has been well described.

The term "MHC binding motif" is intended to mean the amino acids of the variable region, (i.e. polymorphic) of an MHC class II molecule, which can contact and bind the peptide of the invention in the peptide-binding site. The variable region of an MHC class II molecule being defined as the first amino acid residues 1-90 of the alpha and the beta chain in the form seen on the cell surface.

The term "variable region on the MHC molecule" is intended to mean the first domain of both alpha and beta chains each encompassing amino acids 1-90.

The term "constant region on a MHC or Ig molecule" is intended to mean the part of the MHC class II molecule that is not part of the variable domains/regions.

The term "carrier" is intended to mean a compound, such as a protein, which can bind to the peptide of the invention and present that particular peptide to specific T cell receptors. T cell receptors (TCR), which normally are bound to T cells normally recognising type II collagen, a joint cartilage protein.

The term "peptide" is intended to mean a sequence of amino acid residues having from six to 50 amino acid residues.

The term "polypeptide" is intended to mean a sequence of amino acid residues having more 51 or more amino acid residues.

In the present context, amino acid names and atom names are used as defined by the Protein DataBank (PDB), which is based on the IUPAC nomenclature (IUPAC Nomenclature and Symbolism for Amino Acids and Pep-tides (residue names, atom names etc.), Eur J Biochem., 138, 9-37 (1984) together with their corrections in Eur J Biochem., 152, 1 (1985). The term "amino acid" is intended to indicate an amino acid from the group consisting of alanine (Ala or A), cysteine (Cys or C) aspartic acid (Asp or D), glutamic acid (Glu or E), phenyl-alanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W) and tyrosine (Tyr or Y), or derivatives thereof.

Description
Compound

The invention relates to a compound, comprising a peptide and a carrier.

Said peptide having at least the motif X-X-X-X-X-X-X, wherein at least one amino acid residue X is glycosylated, such as an O-linked galactose. Other examples of the glycosylated structures are N-acetyl galactosamine, glucose, N-acetyl glucosamine, glucose, mannose, fucose, as well as their mono- and dideoxygenated, mono- and difluorogenated, and C-glycoside derivatives. Said peptide being linked to the carrier and the linking between said peptide and said peptide binding protein may be covalent or they may be bound in another way as long as they can bind and remain bound to each other. The glycosylated amino acid residue X of said peptide may be hydroxylysine or a variant thereof. A variant of the lysine side chain could be any structure that is acceptable for recognition by a T cell receptor, such as hydroxynorvaline. Said peptide may comprise from 4 to 50 amino acid residues, such as 5, 6, 7, 8, 9, 10, 11, 12, 13, 14, 15, 16, 17, 18, 19 or 20 amino acid residues. Said peptide may comprise at least one of the following amino acid sequences X-F-K-X-X-X-X-X-X-X (SEQ. ID. NO.: 12), X-F-K-X-E-X-X-X-X-X (SEQ. ID. NO.: 13), A-G-F-K-G-E-A (SEQ. ID. NO. 5) or A-A-A-K-A-A-A (SEQ. ID. NO.: 6) wherein K may be hydroxylysine. Additionally, said peptide also have a MHC class II binding motif, i.e., have the ability to bind to such a molecule. A MHC class II binding motif is capable of binding to a threedimensional structure formed by the alpha and the beta chains of the first domain of the MHC class II molecule. The amino acids of critical importance for this peptide binding structure are both located in a beta pleated sheath forming the bottom of the peptide binding structure (alpha 1-49, beta 1-49) and two alpha helices (alpha50-80, beta 50-90) forming the sides of these cleft-forming structure.

Peptides forming specific motifs unique for each MHC class II allele binds to this peptide binding structure. MHC class II alleles associated with rheumatoid arthritis forms peptide binding structure with many similarities encompassing them to bind peptides with certain binding motifs. One example of a peptide, according to the invention, is derived from collagen II, positions 260-273 (IAGFKGEQGPKGEP) (SEQ. ID. NO.: 11) which binds the DRB1*0401/DRA, the DRBI*1001/DRA and the DRB1*0101/DRA molecules. However, the peptide may be synthetic or semisynthetic or derived from other proteins as long as the peptide is identical or have similar structure as the peptide above. The MHC binding positions for binding to the DRB1*0401/DRA molecule has been hypothesised to be F263 and E266 in this peptide and the TCR binding positions K264, Q267 and K270. These TCR contacting positions could be of different importance for different TCR, i.e., they could be substituted into other amino acid residues.

Additionally, the above, mentioned peptide (IAGFKGEQGPKGEP) (SEQ. ID. NO. 11) may have one or more modifications such as hydroxylation, galactosylation or galactoglucosylation. Examples of positions, which could be modified, are positions K264 and K270 as well as deamidation of position Q267. Accordingly one or more of the amino acid residues may be substituted with another amino acid residue as long as it have the capability to be part of the MHC binding motif and function as a composition which can be used to prevent/reduce or treat a mammal suffering from a joint inflammatory disease or disorder or induce an immune response and thereby function as a vaccine. Examples of mammals includes human, dog, pig, sheep, cat, camel and horse.

The carrier of the compound to which the peptide is linked comprises at least the variable region of the MHC class II molecule, being defined as the first domains of the alpha and the beta chain, i.e., the first amino acid residues 1-90 of the alpha and the beta chain and a constant region. The alpha and the beta chains being linked to each other, such as by a leucine zipper domain.

The carrier comprises at least at least a MHC binding motif being linked to said peptide. However, one or more amino acid residues may be substituted as long as the carrier can bind the peptide and induce an immune response in a mammal. The variable part may be modified by up to 30 amino acid residues, such as 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid residues. Examples of variable regions are those, which originate form MHC class II molecules DRB1*0401/DRA, DRBI*0402/DRA, DRBI*0403/DRA, DRBI*0404/DRA, DRB1*0405/DRA, DRB1*0406/DRA, DRBI*0407/DRA, DRBI*0408/DRA, DRBI*0409/DRA, DRBI*0410/DRA, DRBI*0101/DRA, DRB1*0102/DRA, DRBI*1001/DRA, DRBI*1002/DRA. Example sequences of one of the sequences to be used are depicted; SEQ NO 1, DRA V domain and SEQ NO 2, DRB1*0401 V domain.

According to one embodiment the compound comprises the above identified peptide and the carrier comprises a variable and a constant region, wherein said variable region comprises a peptide having 80% identity to the polypeptide sequence in its full length shown in SEQ ID NO 1 and a second polypeptide having 80% identity in its full length to the polypeptide sequence shown in SEQ ID NO 2, such as 85, 90, 95 or 100% identity in its foil length to one or both of the polypeptides shown in SEQ ID NO 1 and 2.

The carrier may also contain one or more constant regions, such as the constant regions of the MHC class II molecule or regions of an immunoglobulin such as the constant regions of IgG. For example, the class II first domain (i.e the variable or polymorphic domain) can be covalently linked to the IgG structure changing the first V domains of the VH and the VL chains. The constant and the variable regions may be covalently linked to each other. Said constant region may be selected from the group consisting of the constant region of an MHC class II molecule or an immunoglobulin. Example of a constant region being one comprising a peptide having 80% identity to the polypeptide sequence in its full length shown in SEQ ID NO 3 and a second polypeptide having 80% identity in its full length to the polypeptide sequence shown in SEQ ID NO 4, such as having 90% or 95% identity to the polypeptide sequence in its foil length shown in SEQ ID NO 3 and a second polypeptide having 90% or 95% identity in its foil length to the polypeptide sequence shown in SEQ ID NO 4 or being identical to the polypeptide sequence shown in SEQ ID NO 3 and 4.

In another embodiment, the constant region of the carrier may be a polypeptide sequence which is at least 25% of the polypeptide sequences SEQ ID NO 3 and 4, i.e., the constant region of the MHC class II, such as 30%, 40%, 50%, 60%, 70%, 80%, 90% or 100%. Additionally there may be one or more substitutions of the polypeptides as long as the polypeptide sequences are linked together to form a carrier as defined above. The polypeptide sequences may be covalently linked to each other through a leucine zipper domain or part of a leucine zipper domain.

```
SEQ ID NO 1:
DR alpha V domain:
IKEEHVIIQAEFYLNPDQSGEFMFDFDGDEIFHVDMAKKETVWRLEE

FGRFASFEAQGALANIAVDKANLEIMTKRSNYT

SEQ ID NO 2:
The DR beta V domain (from DRB1*0401)
GDTRPRFLEQVKHECHFFNGTERVRFLDRYFYHQEEYVRFDSDVGEY

RAVTELGRPDAEYWNSQKDLLEQKRAAVDTYCRHNYGVGESFT

SEQ ID NO 3:
DR alpha constant domain to be used:
PITNVPPEVTVLTNSPVELREPNVLICFIDKFTPPVVNVTWLRNGKP

VTTGVSETVFLPREDHLFRKFHYLPFLPSTEDVYDCRVEHWGLDEPL

LKHWEFDAPSPLPETTEN

SEQ ID NO 4:
DR beta (from DRB1*0401) constant domain to be
used:
VQRRVYPEVTVYPAKTQPLQHHNLLVCSVNGFYPGSIEVRWFRNGQE

EKTGVVSTGLIQNGDWTFQTLVMLETVPRSGEVYTCQVEHPSLTSPL

TVEWRARSESAQS
```

A Pharmaceutical Composition

According to another aspect the invention relates to a pharmaceutical composition comprising above defined compound and a pharmaceutically acceptable carrier, excipient or diluter.

Pharmaceutical formulations of the compound of the invention are typically administered in a composition that includes one or more pharmaceutically acceptable carriers and diluters. Such pharmaceutical compositions may be prepared in a manner known in the art that is sufficiently storage stable and suitable for administration to humans and animals. The pharmaceutical composition may be lyophilised.

"Pharmaceutically acceptable" means a carrier, diluent or excipient that at the dosage and concentrations employed does not cause any unwanted effects in the patients to whom it is administered. Such pharmaceutically acceptable carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

The pharmaceutical composition may be admixed with adjuvants such as lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, they may be dissolved in saline, water, polyethylene glycol, propylene glycol, ethanol, oils (such as corn oil, peanut oil, cottonseed oil or sesame oil), tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be subjected to conventional pharmaceutical operations such as sterilisation and/or may contain conventional adjuvants such as preservatives, stabilisers, wetting agents, emulsifiers, buffers, fillers, etc., e.g., as disclosed elsewhere herein.

The pharmaceutical composition according to the invention may be administered locally or systemically such as topically, intravenously, orally, parenterally or as implants and even rectal use is possible. Suitable solid or liquid pharmaceutical preparation forms are, for example granules, powders, tablets, coated tablets, (micro) capsules, suppositories, syrups, emulsions, suspensions, creams, aerosols, drops or injectable solution in ampule form and also preparations with protracted release of active compounds, in the preparation of excipients, diluents, adjuvants or carriers are customarily used as described above.

The pharmaceutical composition will be administered to a patient in a pharmaceutically effective dose. By "pharmaceutically effective dose" is meant a dose that is sufficient to produce the desired effects in relation to the condition for which it is administered. The exact dose is dependent on the activity of the compound, manner of administration, nature and severity of the disorder, age and body weight of the patient and different doses may be needed. The administration of the dose can be carried out both by single administration in the form of an individual dose unit or else several smaller dose units and also by multiple administration of subdivided doses at specific intervals, e.g. vaccination.

The pharmaceutical composition of the invention may be administered alone or in combination with other therapeutic agents. These agents may be incorporated as part of the same pharmaceutical composition or may be administered separately. The "patient" for the purposes of the present invention includes both humans and other mammals. Thus the methods are applicable to both human therapy and veterinary applications.

Pharmaceutical formulations of the nucleotide sequence molecule or polypeptide of the invention are typically administered in a composition that includes one or more pharmaceutically acceptable carriers or excipients. Such pharmaceutical compositions may be prepared in a manner known in the art that is sufficiently storage stable and suitable for administration to humans and animals.

In a final aspect the above mentioned compound as well as pharmaceutical composition may be used for the treatment of a disease or a disorder such as an inflammatory joint disease threw vaccination. Examples of diseases are arthritis, reumatoid arthritis, anylosing spondylitis, psoriasis arthritis, osteoarthritis, relapsing polychondritis and Menieres disease. The vaccination may be performed by the use of any vaccination system such as DNA vaccination in which DNA is used that is translated into proteins in vivo corresponding to the above described structures. The said DNA can be administered as pure DNA or inserted into carrier structures.

Following examples are intended to illustrate, but not to limit, the invention in any manner, shape, or form, either explicitly or implicitly.

EXAMPLES

Example I

Design of the MHC Class II $A^q$ Constructs

The cDNAs for Aalpha$^q$ and Abeta$^q$ were amplified from a first strand cDNA reaction (first strand cDNA, Pharmacia, Piscataway, N.J.). The cDNAs were further modified to include cloning sites immediately upstream of the start codon, and the 3' end from the transmembrane domain and downstream was replaced by an inframe cloning site. Next, DNA for the leucine zipper (13) domain from Jun including a 3' end coding for 6 histidines was cloned in frame with the beta-chain cDNA. The DNA for the leucine zipper domain from Fos was added to the alpha chain construct. The resulting constructs were cloned separately into pMTAL (Invitrogen, La Jolla, Calif.) or pRmHa-3 (14) to allow for heavy metal-induced expression in insect cells. pMTAL contains the resistance gene for hygromycin. Where pRmHa-3 was used a Copia promoter-driven hygromycin gene was used as selection marker.

Example 2

Transfection, Expression and Purification of Soluble $A^q$

The linearised $A^q$ alpha-chain and $A^q$ beta-chain constructs were co-transfected at equimolar ratios into *Drosophila melanogaster* SL2 cells (ATCC, CRL-1963) using calcium phosphate transfection. Stable transfectants were derived by hygromycin selection and kept under selection in Schneider's *Drosophila* medium (Gibco™, Paisley, Scotland, UK) containing 100 µg/ml of hygromycin B (Sigma-Aldrich Chemie GmbH, Steinheim, Germany). Large-scale cell cultures were prepared in Fernbach bottles using a magnetic stirrer. For expression of soluble $A^q$, transfected cells were grown in serum-free Insect express complete medium (PAA Laboratories GmbH, Linz, Austria) at 25° C., induced with 0.7 mM CuSO4 for three days, and the supernatants were clarified by centrifugation and filtration. The SL2 cells produced ~2-3 mg of recombinant protein per liter of culture. The expressed soluble $A^q$ molecules were purified from the clarified media using Ni-NTA (Qiagen GmbH, Hilden, Germany) affinity chromatography and the manufacturer's recommended protocol. The dialysed protein fractions were examined by ELISA, SDS-PAGE and Western blot analysis. Non-reducing SDS-PAGE analysis of NiNTA purified $A^q$ on 4-20% gradient gel showed two bands with molecular weights of 29 and 33 kDa (approximately the predicted sizes of alpha and β beta chains), which demonstrates that the expressed proteins form heterodimers consisting of alpha and beta chains. Positive fractions were pooled, concentrated 5- to 10-fold by MICROSEP 30K OMEGA (PALL, GelmanSciences, Ann Arbor, Mich.) or Amicon® centrifugal filter devices (MILLIPORE Co, Billerica, Mass.) and loaded with a peptide to form MHC-peptide complexes. All protein concentrations were determined using a Dc protein assay (Bio-Rad Laboratories, Hercules, Calif.).

Example 3

ELISA, SDS-PAGE and Western Blot Analyses of $A^q$

The alpha- and beta-chains of the purified $A^q$ protein were detected by sandwich ELISA, using Y3P mAb (specific for the native alpha-chain) as capturing antibodies and biotinylated 7-16.17 (BD PharMingen, Los Angeles, Calif.) mAb (specific for the beta-chain) as detecting antibodies. Flat-bottom 96-well plates (Nunc, Roskilde, Denmark) were coated with 2.5 g/mL Y3P and incubated overnight at 4° C. The plates were then washed with PBS, blocked with 1% BSA (Sigma, St Louis, Mo.) in PBS for 1 h, washed again, and incubated for 2 h with 50 µL from the protein fractions at room temperature. Plates were washed again, followed by addition of 1 µg/mL biotinylated 7-16.17 for 1 h. After washing, the biotin-labeled antibody was detected by europium-labeled streptavidin using the DELFIA system (Wallac, Turku, Finland).

Protein purity was assessed by SDS-PAGE. Samples were electrophoresed in 4-20% polyacrylamide gradient ready mini-gels (Bio-Rad Laboratories, Hercules, Calif.) under denaturing and non-reducing conditions and the gels were silver stained according to the manufacturer's instructions. In parallel experiments, the gels were electrotransferred onto nitrocellulose membranes (0.45 µm). The membranes were blocked in 5% non-fat dry milk in PBS for 1 h and blotted with different MHC class II specific antibodies (M5/114, 7-16.17, 7-23.1, PCQ.6, 34-5-3, Y3P) at 4° C. overnight. After repeated washing, blots were incubated with peroxidase-conjugated goat anti-mouse IgG or goat anti-rat IgG (for M5/114) antibodies (Jackson) for 1 h. Immunoblots were developed using DAB (Vector Laboratories Inc., Burlingame, Calif.).

Example 4

Preparation of Peptide/$A^q$ Complexes

Empty soluble $A^q$ molecules were loaded with 5 to 50-fold molar excess of GalOK264 CII259-273, non-modified CII259-273 or MOG79-90 peptides at 4° C. for 72 h. GalOK264 CII259-273 is a peptide from type II collagen (CII) position 259-273 which has a lysine at position 264, which is hydroxylated and galactosylated.

Non-modified is the same peptide but with a lysine without modifications of its side chain. MOG=myelin oligodendrocytic glycoprotein. MHC-peptide complexes were separated by anion-exchange HPLC (Resource™ Q column) using an ÄKTA™ explorer 100 Air system (Amersham Pharmacia Biotech AB, Uppsala, Sweden) with UNICORN V4.00 software. Separations were done with a loading solution of 10 mM Tris pH 8.5 (buffer A) and a gradient elution up to 1 M NaCl (buffer B) in 10 mM Tris. The eluted protein fractions were concentrated by ultrafiltration (MICROSEP 30K OMEGA), dialyzed against PBS and examined by ELISA, SDS-PAGE and T-cell hybridoma tests. MHC-peptide complexes were purified further on a Superdex 200 gel filtration column (Amersham Pharmacia Biotech AB, Uppsala, Sweden), concentrated again by Amicon® centrifugal filter devices (MILLIPORE Co, Billerica, Mass.) and stored at −20° C. until used.

Example 5

Activation of T Cell Hybridomas

Figure 2:
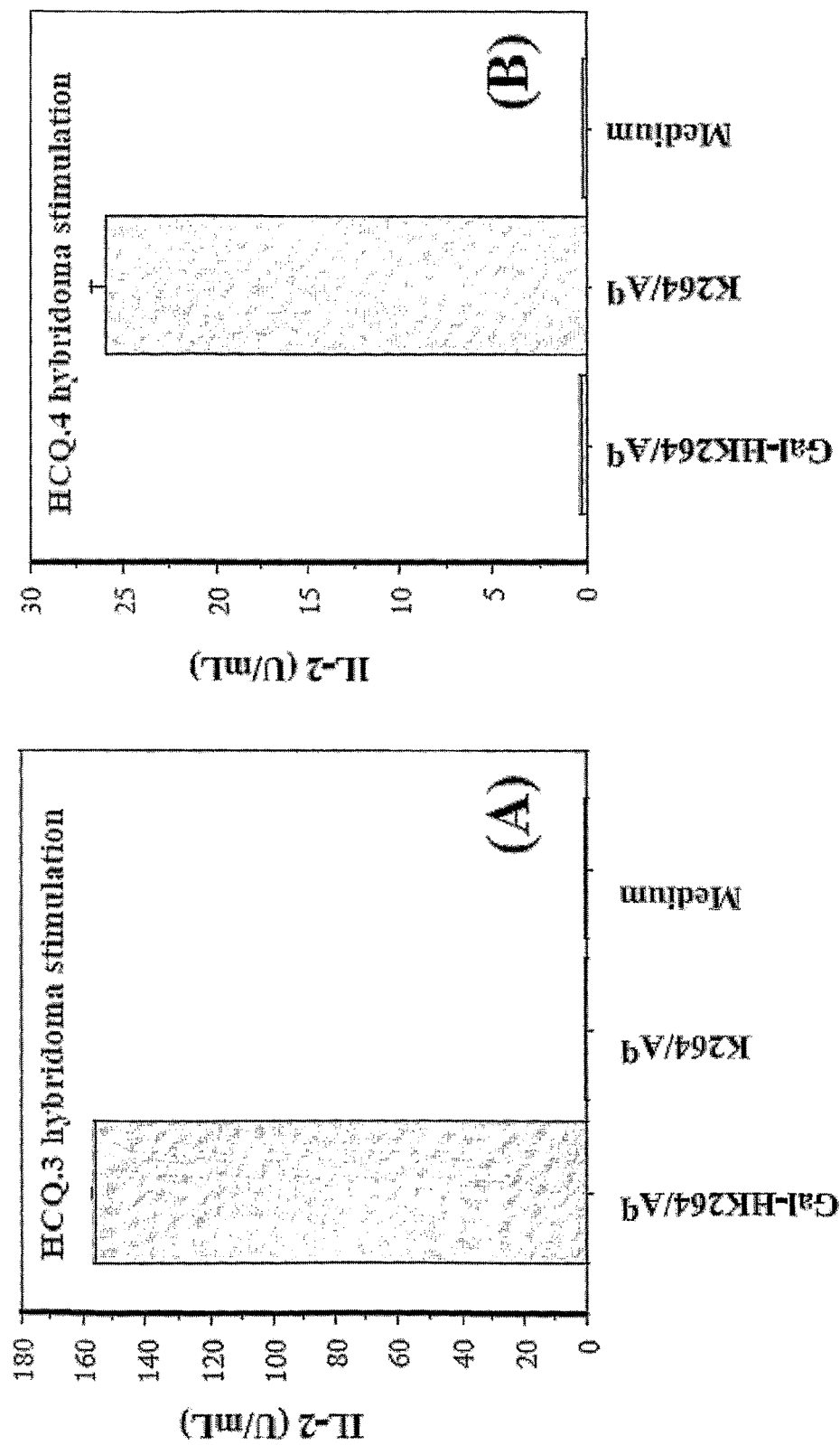
FIG. 2 shows a criss-cross test of T-cell hybridoma specificities for peptide/Aq complexes. (A) HCQ.3 hybridoma, specific for GalOK264 CII259-273 epitope; (B) HCQ.4 hybridoma, specific for non-modified (K264) CII259-273 epitope.

Peptide/$A^q$ complexes were diluted in sterile PBS and coated onto plates by incubation at 4° C. for overnight or added directly in soluble form to the hybridomas. The coated plates were then washed twice with sterile PBS to remove unbound protein complexes, and $5 \times 10^4$ T-hybridoma cells were added per well in 200 µL of DMEM supplemented with 5% FCS, 100 IU/mL penicillin and 100 µg/mL streptomycin. T-cell hybridoma HCQ.3 and HCQ.4, specific for GalOK264 and for non-modified CII259-273 (K264), respectively (12), have been used in FIG. 1. To block the activation of the hybridomas, 5 µg/ml of 7-16.17 antibodies were added to the immobilised complexes. In the criss-cross test (FIG. 2) five µg/ml of soluble peptide/Aq complexes were added directly (without coating) to HCQ.3 and HCQ.4 hybridoma cells (5×104). Medium alone (without antigen) was used as a negative control.

After 24 h, IL-2 in the culture supernatants was measured by sandwich ELISA using DELFIA system (Wallac, Turku, Finland). Recombinant mouse IL-2 served as a positive control and standard. Data are represented as mean+−SE of triplicates Example 6

Induction and Clinical Evaluation of Arthritis
Animals

Male B10.Q, (B10.Q×B10.RIII)FI or B10.Q×(BALB/c× B10.Q)F2 mice, 8-10 weeks of age, were used in the experiments. The founders of the B10.Q and B10.RIII mice were originally provided by Dr. Jan Klein (Tubingen, Germany) and BALB/c mice purchased from The Jackson Laboratory (Bar Harbor, Me.). The mice were bred and used at the animal department of Medical Inflammation Research (http://www.inflam.lu.se) and kept under standardized conditions.

Figure 3:
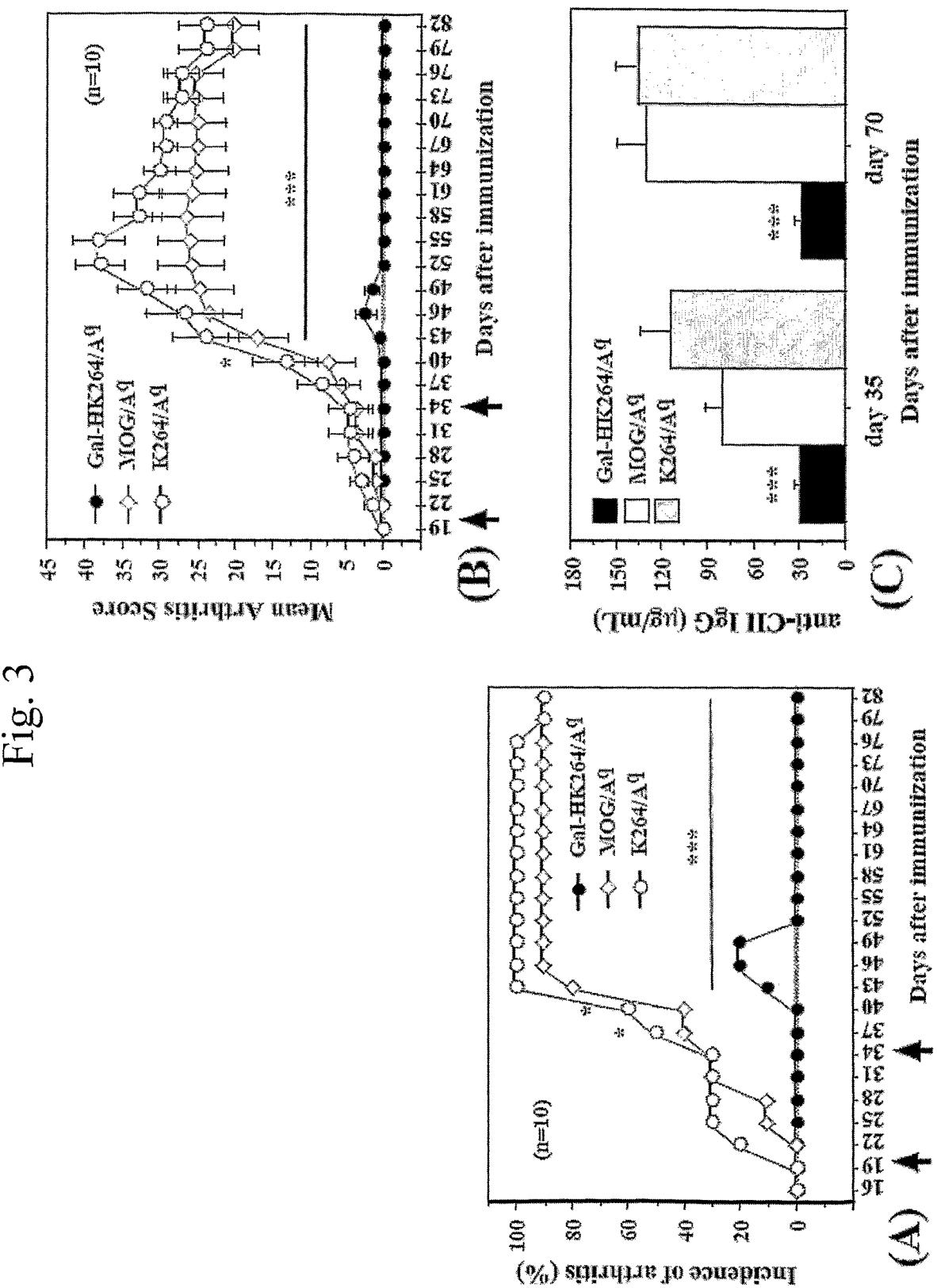
FIG. 3 shows that GalOK264/Aq complexes suppress development of CIA. (A) Incidence of arthritis (percent of affected mice); (B) Mean clinical score of arthritis severity including both arthritic and healthy mice; (C) Anti-CII IgG serum levels. All data represent mean±SE of 10 mice per group. *, $p<0.05$; , $p<0.0I$ and *, $p<0.001$.

In FIG. 3 is used B10.Q mice (10 animals per group), which were immunised with 100 µg rat CII in CFA on day 0 and boosted on day 35 with 50 µg rat CII in IFA. On days 20 and 34 (arrows), mice were treated by intravenous administration of purified peptide/Aq complexes (100 µg in 200 µl PBS). Sample sera were collected at days 35 and 70 after immunisation and incubated in serial dilutions in rat CII-coated wells. Levels of IgG anti-CII antibodies were measured by ELISA.

Figure 4:
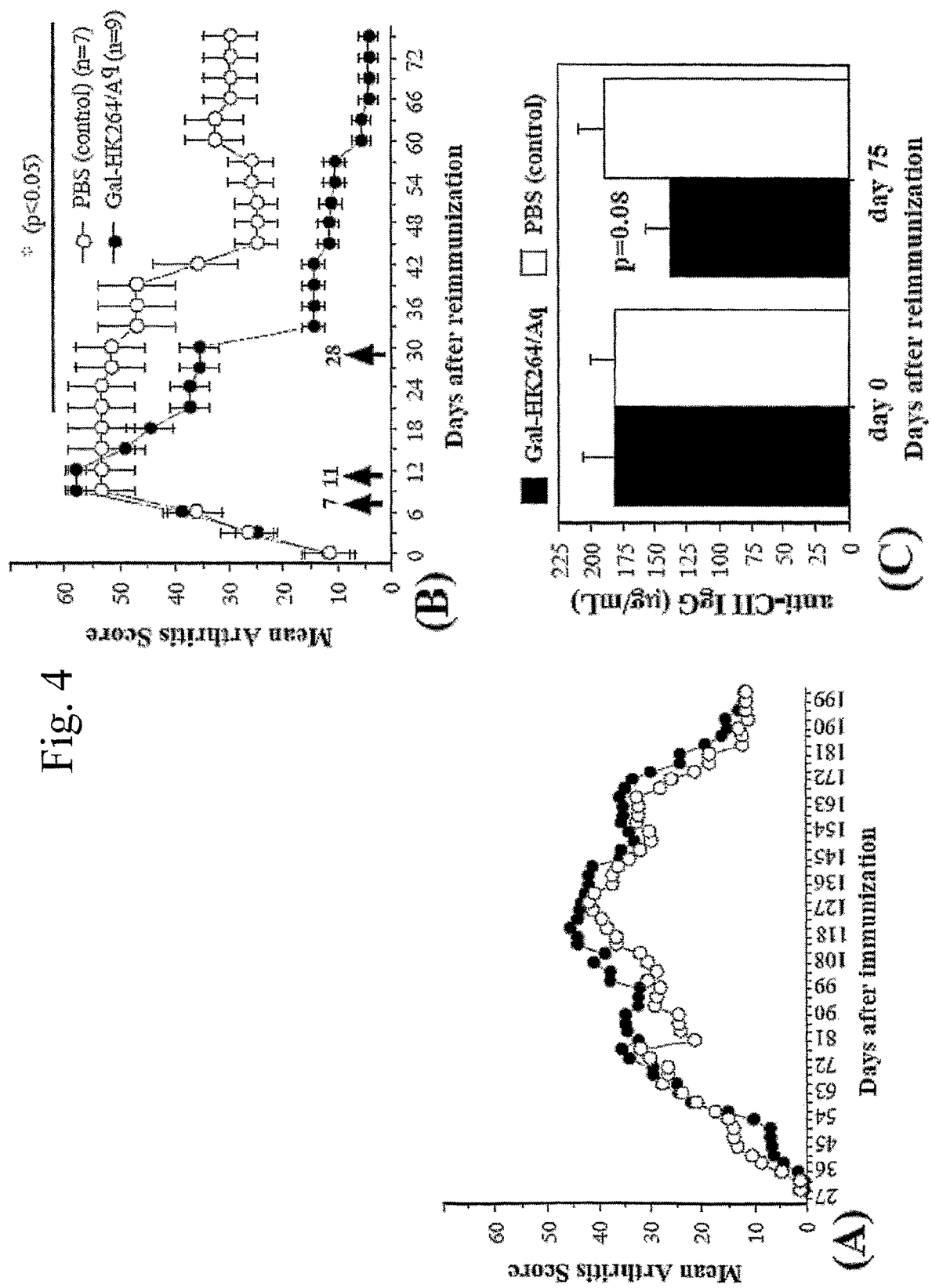
FIG. 4 shows that GalOK264/$A^q$ complexes reduce arthritis progression in chronic stage. (A) Mean arthritis score for 202 days of the chronic mice chosen for treatment; (B) Mean clinical score of GalOK264/$A^q$ treated mice after reimmunisation; (C) Anti-CII IgG serum levels.

In FIG. 4 is used B10.Q(BALB/c×B10.Q)FI mice were immunised with 100 µg of rat CII emulsified in IFA on day 0 at the base of the tail and boosted on day 35 with 50 µg of rat CII in IFA. The mice were scored for a period of 202 days for arthritis development. Mice, which developed chronic arthritis were selected for the treatment experiment. All selected animals were reimmunised on day 205 (day 0 of the reimmunisation) with 50 µg rat CII in IFA and scored the next 75 days for clinical signs of arthritis. On days 7, 11 and 28 after reimmunisation (arrows), mice were treated by intravenous (100 µg in 200 ul PBS) administration of purified GalOK264/$A^q$ complexes (10 mice in this group). PBS was administrated (i.v.) as a control on the same days (7 mice in this group). Sample sera were collected at days 0 and 75 after reimmunisation and measured by ELISA. Data are represented as mean±SE.

Figure 5:
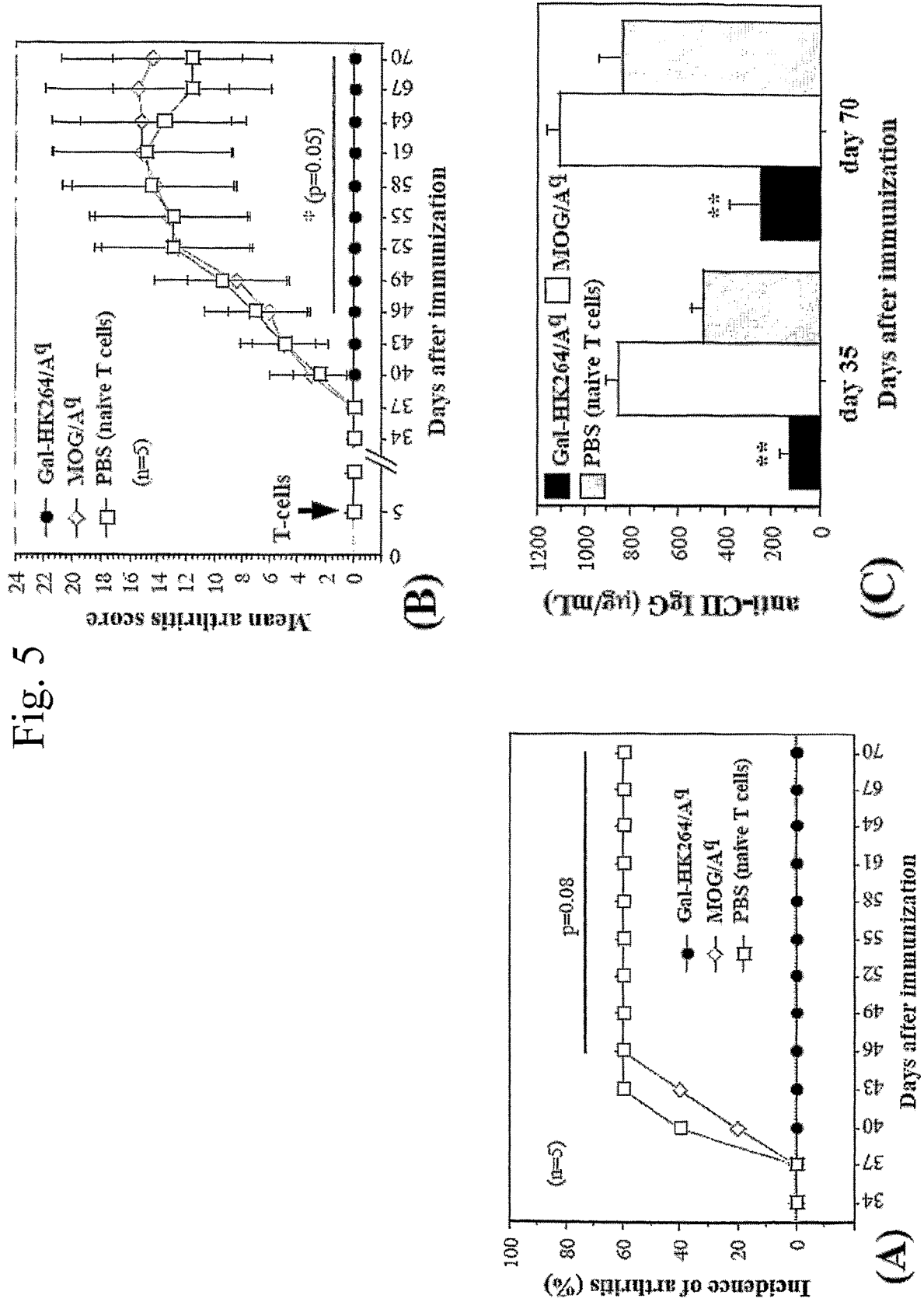
FIG. 5 shows transfer of T cells from GalOK264/$A^q$ treated mice provided protection against CA development. (A) Mean clinical score of arthritis after T-cell transfer; (B) Anti-CII IgG serum levels.

In FIG. 5 three groups of donor B 10. Q mice (5 mice in each group) were injected i.v. with 200 ug GalOK264/$A^q$ in 100 ul PBS, 200 µg MOG/$A^q$ in 100 µl PBS or 100 µl PBS alone. Five days later, T cells were purified from each mouse individually by negative selection and transferred i.v. ($1 \times 10^6$ cells per mouse) to the CII-immunised recipients (5 days after immunisation). Sample sera were collected at days 35 and 70 after immunization measured by ELISA. Results are expressed as the mean±SE.

Figure 6:
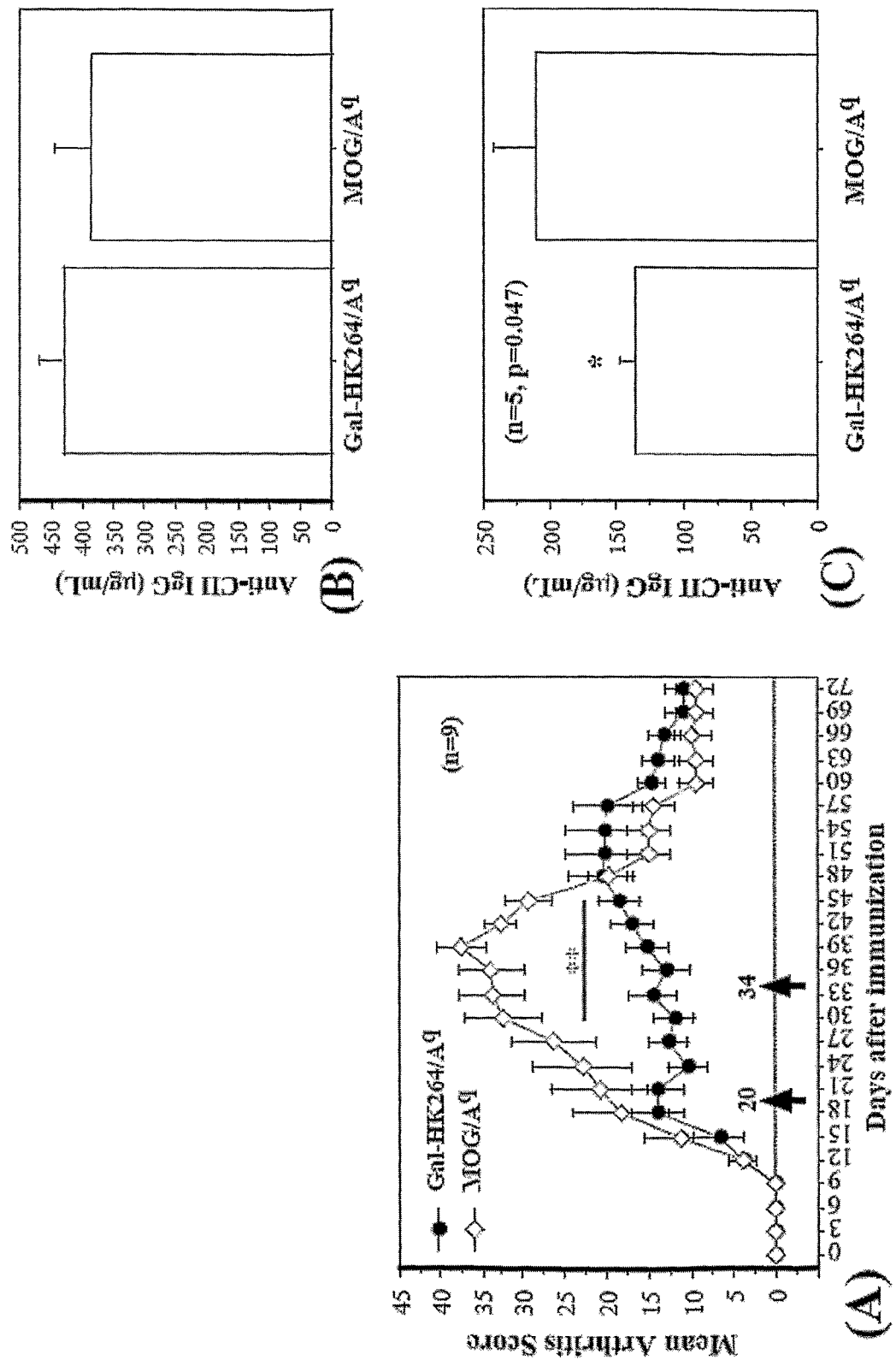
FIG. 6 shows that GalOK264/$A^q$ treatment blocked arthritis progression in H2q/r FI mice.

In FIG. 6 are (B10.Q×B10.RIII)FI mice immunised at day 0 with bovine CII. On days 20 and 34 (arrows), the mice were treated by intravenous administration of purified peptide/$A^q$ complexes (100 µg in 200 µl PBS (9 mice per group) (A). Sample sera were collected at days 35 and 70 after immunisation and measured for levels of anti-CII antibodies by ELISA (B). In another experiment, (B10.Q×B10.RIII)FI mice (5 mice per group) were administrated once with 200 µg in 200 µl PBS peptide/$A^q$ complexes at the day of immunisation (day 0) and sera were collected at day 18 (C). All data represent mean±SE. *, p<0.05; **, p<0.01.
Antigens Rat type II collagen (CII) was prepared from the Swarm chondrosarcoma and bovine CII from joint cartilage, by limited pepsin digestion, and further purified as previously described (15). The CII peptides (non-modified CII259-273: GIAGFKGEQGPKGEP (SEQ. ID. NO.: 8), GalOK264 CII259-273: GIAGFK(Gal-Hyl)GEQGPKGEP (SEQ. ID. NO.: 9), and the various galactosylated peptides that were deoxygenated at OH groups on the galactose (position 2, 3 and 4 respectively) were synthesized, purified and characterized as previously described (9, 10, 11, 16, 17). The CII was dissolved in 0.1 M acetic acid. Mouse myelin oligodendrocytic glycoprotein MOG79-90 peptide (GKVTL-RIQNVRF) (SEQ. ID. NO.: 10) was purchased from Schafer-N(Copenhagen, Denmark). All peptides were dissolved in PBS. The collagen and peptides were stored at 4° C. until used.

To induce CIA, each mouse was injected with 100 µg of CII (rat CII for B10.Q and bovine CII for (B10.Q×B10.RIII) FI mice), emulsified 1:1 in complete Freund's adjuvant (CFA; Difco, Detroit, Mich.) at the base of the tail in a total volume of 100 µl. Thirty-five days later, the mice were given a booster injection of 50 µg of rat CII emulsified 1:1 in incomplete Freund's adjuvant (IFA; Difco, Detroit, Mich.) in a total volume of 50 µl. Development of clinical arthritis was followed through visual scoring of the animals based on the number of inflamed joints in each paw, starting two weeks postimmunisation and continuing until the end of the experiment. An extended scoring protocol (18) ranging from 1-15 for each paw with a maximum score of 60 per mouse was used. The mice were examined 2 to 4 times a week for at least 70 days after immunization.

The B10.Q(BALB/c×B10.Q)F2 mice were immunized with 100 µg of rat CII emulsified in IFA intradermally (i.d.) at the base of the tail on day 0 and boosted on day 35 i.d. with 50 µg of rat CII in IFA. The mice were scored for a minimum period of 202 days for arthritis development. Mice, which developed chronic arthritis (mice with severe arthritis for a minimum period of 120 days were considered as chronic) including the ones with clear relapses, were selected for the treatment protocol.

Peptide/A$^q$ Complex Treatment Protocols

Animals were treated by either intravenous (i.v.) or intranasal (i.n.) administration of purified peptide/A$^q$ complexes. In the intravenous treatment of CIA model, mice were injected with GalOK264/A$^q$, deoxygenated GalOK264/A$^q$, K264/A$^q$ or as negative control MOG/A$^q$ complex (100 µg in 200 µL PBS) on days 20 and 34 postimmunisation (for the chronic model on days 7, 11 and 28 after reimmunisation). Control mice were injected intravenously with 200 µL PBS on the same days. In the intranasal treatment experiments, mice were administrated with 10 µg (in 20 µL PBS) of peptide/A$^q$ complex on the days mentioned above.

Example 6

Measurement of Serum Anti-CII Antibody Levels

Mice were bled at the time of boost immunization (day 35) as well as at the termination of experiment (day 70) and sera were analyzed for anti-CII IgG antibody levels by quantitative ELISA (19). Briefly, 96-well ELISA plates (Nunc, Roskilde, Denmark) were coated overnight at 4° C. with 10 µg/mL native rat CII in PBS. The wells were washed three times with PBS-0.1% Tween 20 and then 150 µL of blocking buffer (5% BSA in PBS) was added to each well and incubated for 1 h at room temperature. After washing, 50 µL of samples in serial dilutions from 1/100 to 1/10$^5$ were added and incubated for 2 h at room temperature. After three washes, peroxidase-conjugated goat anti-mouse IgG was added and incubated at room temperature for 1 h. After extensive washing, plates were developed using ABTS (Roche Diagnostics GmbH, Mannheim, Germany) as substrate and the absorbance was then measured at 405 nm in a Spectra Max Plus reader (Göteborgs Termometerfabrik, Göteborg, Sweden). A standard serum from arthritic and non-immunised syngeneic mice was added to each plate in serial dilutions as positive and negative controls, respectively.

TABLE 1

Peptide/A$^q$ complexes suppress development of CIA in B10.Q mice.

| Treatment | Incidence | Mean day of onset | Mean peak of severity | Mean anti-CII IgG (µg/mL) | |
|---|---|---|---|---|---|
| | | | | day 35 | day 70 |
| GalOK264/A$^q$(i.v.) | 0/10 (0%) | N/A | N/A | 54.3 ± 10.5 | 36.9 ± 10.5 |
| GalOK264/A$^q$(i.n.) | 1/10 (10%) | 60 | 2 | 59.8 ± 15.4 | 38.8 ± 15.8 |
| PBS (control)(i.v.) | 8/10 (80%) | 44 +/− 5 | 26.2 +/− 15.4 | 135.9 ± 30.9 | 96.6 ± 35.1 |

B10.Q mice (10 mice per group) were immunised with 100 microgrammes rat CII in CFA on day 0 and boosted on day 35 with 50 microgrammes rat CII in IFA. On days 20 and 34, mice were treated by intravenous (i.v.) (100 microgrammes in 200 microlitres PBS) or intranasal (i.n.) (10 microgrammes in 20 microlitres PBS) administration of purified GalOK264/Aq complex. PBS (200 microlitres) was administered (i.v.) as a control on the same days. Mice were monitored for clinical signs of arthritis for 70 days. Levels of IgG anti-CII were measured at days 35 and 70 by ELISA. All values are shown as mean±standard deviation. N/A denotes not applicable.

Example 7

Histology

Hind paws were removed after ending the experiment, fixed in 4% neutral buffered formaldehyde overnight and then decalcified in 5% (w/v) EDTA at 4° C. until the bones were pliable. Tissues were then dehydrated in a gradient of alcohols, paraffin embedded, sectioned at 5 µm, mounted on glass slides, and stained with hematoxylin and eosin (H&E). Serial H&E-stained sections were analyzed microscopically for the degree of inflammation and for cartilage and bone destruction. Analyses were performed in a blinded fashion.

Example 8

T-cell transfer

For the T-cell transfer experiment, 15 B10.Q mice (recipients) were immunized with CII/CFA (day 0) and boosted with CII/IFA on day 35 using the standard immunization protocol. At the same time (day 0), three groups (5 mice per each group) of other B10.Q mice (donors) were injected i.v. with 200 µg GalOK264/Aq in 100 µl PBS, 200 µg MOG/Aq in 100 µl PBS or 200 µl PBS alone, respectively. Five days later, erythrocyte free spleen and lymph node cells from each mouse were passed through 40 µm nylon cell strainer (BD Biosciences Discovery Labware, Bedford, Mass.) and then T cells were purified by negative selection using antibodies against MHC class II+(M5/114) and CDIIb+(MI/70) expressing cells (BD Biosciences PharMingen, San Diego, Calif.) and Dynabeads® (Dynal ASA, Oslo, Norway) followed by magnetic sorting. The purity of the resulting T cells was measured by flow cytometry and were found to be contaminated with <0.3% MHC II+ expressing cells. Purified T cells were analysed by FACS for expression of CD25+, CD62L+, CD45RB+ and NK 1.1+ surface markers but no differences between the individual mice or groups were found. Purified T cells (1×10$^6$) from each individual donor were resuspended in a final volume of 200 µl sterile PBS and transferred intravenously into recipient mice.

Statistics

Statistical difference in the incidence of disease between groups of mice described in the examples was determined using Chi Square test. To compare nonparametric data for statistical significance, we applied the Mann-Whitney U or Kruskal Wallis test on all clinical results and in vitro experiments using the StatView™ programme (SAS, Institute Inc., USA).

REFERENCES

1. Aho, K., Palosuo, T., Raunio, V., Puska, P., Aromaa, A. & Salonen, J. T. (1985) *Arthritis Rheum* 28, 485-489.
2. Rantapaa-Dahlqvist, S., de Jong, B. A., Berglin, E., Hallmans, G., Wadell, G., Stenlund, H., Sundin, U. & van Venrooij, W. J. (2003) *Arthritis Rheum* 48, 2741-9.
3. Berglin, E., Padyukov, L., Sundin, U., Hallmans, G., Stenlund, H., Van Venrooij, W. J., Klareskog, L. & Dahlqvist, S. R. (2004) Arthritis Res Ther 6, R303-8.
4. van Gaalen, F. A., van Aken, J., Huizinga, T. W., Schreuder, G. M., Breedveld, F. C., Zanelli, E., van Venrooij, W. J., Verweij, C. L., Toes, R. E. & de Vries, R. R. (2004) *Arthritis Rheum* 50, 2113-21.
5. Corrigall, V. M., Bodman-Smith, M. D., Fife, M. S., Canas, B., Myers, L. K., Wooley, P., Soh, C, Staines, N. A., Pappin, D. J., Berlo, S. E., van Eden, W., van Der Zee, R., Lanchbury, J. S. & Panayi, G. S. (2001) *J Immunol* 166, 1492-8.

6. Fritsch, R., Eselbock, D., Skriner, K., Jahn-Schmid, B., Scheinecker, C, Bohle, B., Tohidast-Akrad, M., Hayer, S., Neumuller, J., Pinol-Roma, S., Smolen, J. S. & Steiner, G. (2002) *J Immunol* 169, 1068-76.
7. Cook, A. D., Rowley, M. J., Mackay, I. R., Gough, A. & Emery, P. (1996) *Arthritis Rheum* 39, 1720-1727.
8. Bäcklund, J., Carlsen, S., H[delta]ger, T., Holm, B., Fugger, L., Kihlberg, J., Burkhardt, H. & Holmdahl, R. (2002) *Proc Natl Acad Sci USA* 99, 9960-9965.
9. Michaelsson, E., Andersson, M., Engström, A. & Holmdahl, R. (1992) *Eur J Immunol* 22, 1819-25.
10. Holm, B., Backlund, J., Recio, M. A., Holmdahl, R. & Kihlberg, J. (2002) Chembiochem 3, 1209-1222.
11. Holm, B., Baquer, S. M., Holm, L, Holmdahl, R. & Kihlberg, J. (2003) Bioorganic and Medicinal Chemistry 11, 3981-7.
12. Corthay, A., Backhand, J., Broddefalk, J., Michaelsson, E., Goldschmidt, T. J., Kihlberg, J. & Holmdahl, R. (1998) *Eur J Immunol* 28, 2580-2590.
13. Scott, C. A., Garcia, K. C, Carbone, F. R., Wilson, I. A. & Teyton, L. (1996) *J Exp Med* 183, 2087-95.
14. Bunch, T. A., Grinblat, Y. & Goldstein, L. S. (1988) Nucleic Acids Res 16, 1043-61.
15. Andersson, M. & Holmdahl, R. (1990) *Eur J Immunol* 20, 1061-1066.
16. Broddefalk, J., Bäcklund, J., Almqvist, F., Johansson, M., Holmdahl, R. & Kihlberg, J. (1998) *J Am Chem Soc* 120, 7676-7683.
17. Holm, B., Broddefalk, J., Flodell, S., Wellner, E. & Kihlberg, J. (2000) Tetrahedron 56, 1579-1586.
18. Holmdahl, R., Carlsen, S., Mikulowska, A., Vestberg, M., Brunsberg, U., Hansson, A.-S., Sundvall, M., Jansson, L. & Pettersson, U. (1998) in Human Genome Methods, ed. Adolpho, K. W. (CRC press, New York), pp. 215-238.
19. Holmdahl, R., Klareskog, L., Andersson, M. & Hansen, C. (1986) Immunogenetics 24, 84-89.

The invention claimed is:

1. A compound comprising (a) a peptide and (b) a carrier, wherein said peptide is bound within the peptide-binding site of said carrier, and a. said peptide consists of IAGFKGEQGPKG (SEQ. ID. NO.: 7), wherein at least the lysine at position 5 of said peptide is a glycosylated hydroxylysine, and b. said carrier comprises at least the variable region of a naturally occurring MHC class II molecule wherein said carrier does not comprise the transmembrane domain and cytoplasmic domain of the alpha and beta chains of said naturally occurring MHC class II molecule and said alpha and beta chains are linked to each other by a leucine zipper or an immunoglobulin, and wherein said carrier comprises the variable region of an MHC class II molecule selected from the group consisting of DRB1*0401/DRA, DRB1*0101/DRA, and DRB1*1001/DRA.

2. The compound according to claim 1, wherein at least one lysine of said peptide (a) is O-linked glycosylated.

3. The compound according to claim 1, wherein said peptide (a) is covalently bound to said carrier (b).

4. The compound according to claim 1, wherein said carrier comprises a constant region of a MHC class II molecule linked to said variable region of said MHC class II molecule or a constant region of an immunoglobulin linked to said variable region of said MHC class II molecule, wherein said constant region of said MHC class II molecule does not comprise the transmembrane domain and cytoplasmic domain of the alpha and beta chains of said MHC class II molecule.

5. The compound according to claim 4, wherein said constant region of said carrier comprises at least 25% of the polypeptide sequence shown in SEQ ID NO: 3 or SEQ ID NO: 4.

6. The compound according to claim 5, wherein said constant region of said carrier comprises at least 30% of the polypeptide sequences shown in SEQ ID NO: 3 or SEQ ID NO: 4.

7. A pharmaceutical composition comprising
a compound comprising a peptide consisting of IAGFKGEQGPKG (SEQ. ID. NO.: 7), wherein at least the lysine at position 5 of said peptide is a glycosylated hydroxylysine, and a carrier comprising at least the variable region of a naturally occurring MHC class II molecule, wherein said carrier does not comprise the transmembrane domain and cytoplasmic domain of the alpha and beta chains of said naturally occurring MHC class II molecule and said alpha and beta chains are linked to each other by a leucine zipper or an immunoglobulin, and said peptide is bound within the peptide-binding site of said carrier, and
wherein said carrier comprises the variable region of an MHC class II molecule selected from the group consisting of DRB1*0401/DRA, DRB1*0101/DRA, and DRB1*1001/DRA: and
a pharmaceutically acceptable carrier, excipient or diluter.

8. The compound according to claim 1, wherein at least one amino acid residue K of said peptide (a) is O-linked galactosylated.

9. The compound according to claim 1, wherein said variable region of a naturally occurring MHC class II molecule is a recombinant variable region of a naturally occurring MHC class II molecule.

10. The compound according to claim 1, wherein said carrier comprises the variable region of an MHC class II molecule selected from the group consisting of DRB1*0401/DRA and DRB1*0101/DRA.

* * * * *

SEQUENCE LISTING

```
<160> NUMBER OF SEQ ID NOS: 11

<210> SEQ ID NO 1
<211> LENGTH: 80
<212> TYPE: PRT
<213> ORGANISM: Homo sapiens

<400> SEQUENCE: 1

Ile Lys Glu Glu His Val Ile Ile Gln Ala Glu Phe Tyr Leu Asn Pro
1               5                   10                  15

Asp Gln Ser Gly Glu Phe Met Phe Asp Phe Asp Gly Asp Glu Ile Phe
            20                  25                  30

His Val Asp Met Ala Lys Lys Glu Thr Val Trp Arg Leu Glu Glu Phe
        35                  40                  45

Gly Arg Phe Ala Ser Phe Glu Ala Gln Gly Ala Leu Ala Asn Ile Ala
    50                  55                  60

Val Asp Lys Ala Asn Leu Glu Ile Met Thr Lys Arg Ser Asn Tyr Thr
65                  70                  75                  80

<210> SEQ ID NO 2
<211> LENGTH: 90
<212> TYPE: PRT
<213> ORGANISM: Homo sapiens

<400> SEQUENCE: 2

Gly Asp Thr Arg Pro Arg Phe Leu Glu Gln Val Lys His Glu Cys His
1               5                   10                  15

Phe Phe Asn Gly Thr Glu Arg Val Arg Phe Leu Asp Arg Tyr Phe Tyr
            20                  25                  30

His Gln Glu Glu Tyr Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Leu Leu Glu Gln Lys Arg Ala Ala Val Asp Thr Tyr Cys Arg
65                  70                  75                  80

His Asn Tyr Gly Val Gly Glu Ser Phe Thr
            85                  90

<210> SEQ ID NO 3
<211> LENGTH: 112
<212> TYPE: PRT
```

<213> ORGANISM: Homo sapiens

<400> SEQUENCE: 3

```
Pro Ile Thr Asn Val Pro Pro Glu Val Thr Val Leu Thr Asn Ser Pro
1               5                   10                  15
Val Glu Leu Arg Glu Pro Asn Val Leu Ile Cys Phe Ile Asp Lys Phe
                20                  25                  30
Thr Pro Pro Val Val Asn Val Thr Trp Leu Arg Asn Gly Lys Pro Val
            35                  40                  45
Thr Thr Gly Val Ser Glu Thr Val Phe Leu Pro Arg Glu Asp His Leu
        50                  55                  60
Phe Arg Lys Phe His Tyr Leu Pro Phe Leu Pro Ser Thr Glu Asp Val
65                  70                  75                  80
Tyr Asp Cys Arg Val Glu His Trp Gly Leu Asp Glu Pro Leu Leu Lys
                85                  90                  95
His Trp Glu Phe Asp Ala Pro Ser Pro Leu Pro Glu Thr Thr Glu Asn
                100                 105                 110
```

<210> SEQ ID NO 4
<211> LENGTH: 107
<212> TYPE: PRT
<213> ORGANISM: Homo sapiens

<400> SEQUENCE: 4

```
Val Gln Arg Arg Val Tyr Pro Glu Val Thr Val Tyr Pro Ala Lys Thr
1               5                   10                  15
Gln Pro Leu Gln His His Asn Leu Leu Val Cys Ser Val Asn Gly Phe
                20                  25                  30
Tyr Pro Gly Ser Ile Glu Val Arg Trp Phe Arg Asn Gly Gln Glu Glu
            35                  40                  45
Lys Thr Gly Val Val Ser Thr Gly Leu Ile Gln Asn Gly Asp Trp Thr
        50                  55                  60
Phe Gln Thr Leu Val Met Leu Glu Thr Val Pro Arg Ser Gly Glu Val
65                  70                  75                  80
Tyr Thr Cys Gln Val Glu His Pro Ser Leu Thr Ser Pro Leu Thr Val
                85                  90                  95
Glu Trp Arg Ala Arg Ser Glu Ser Ala Gln Ser
                100                 105
```

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

```
Ala Gly Phe Lys Gly Glu Ala
1               5
```

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

```
Ala Ala Ala Lys Ala Ala Ala
1               5
```

```
<210> SEQ ID NO 7
<211> LENGTH: 12
<212> TYPE: PRT
<213> ORGANISM: Artificial Sequence
<220> FEATURE:
<223> OTHER INFORMATION: Synthetic peptide

<400> SEQUENCE: 7

Ile Ala Gly Phe Lys Gly Glu Gln Gly Pro Lys Gly
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide

<400> SEQUENCE: 8

Gly Ile Ala Gly Phe Lys Gly Glu Gln Gly Pro Lys Gly Glu Pro
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Galactosylated hydrolysine

<400> SEQUENCE: 9

Gly Ile Ala Gly Phe Xaa Gly Glu Gln Gly Pro Lys Gly Glu Pro
1               5                   10                  15

<210> SEQ ID NO 10
<211> LENGTH: 12
<212> TYPE: PRT
<213> ORGANISM: Artificial Sequence
<220> FEATURE:
<223> OTHER INFORMATION: Synthetic peptide

<400> SEQUENCE: 10

Gly Lys Val Thr Leu Arg Ile Gln Asn Val Arg Phe
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic peptide

<400> SEQUENCE: 11

Ile Ala Gly Phe Lys Gly Glu Gln Gly Pro Lys Gly Glu Pro
1               5                   10
```